United States Patent [19]

Pinck

[11] Patent Number: 4,729,468

[45] Date of Patent: Mar. 8, 1988

[54] APPARATUS FOR MONITORING THE CONDITION OF FILAMENTARY BELTS IN CIGARETTE MAKING MACHINES AND THE LIKE

[75] Inventor: Peter Pinck, Gross-Hansdorf, Fed. Rep. of Germany

[73] Assignee: Körber AG, Hamburg, Fed. Rep. of Germany

[21] Appl. No.: 855,163

[22] Filed: Apr. 23, 1986

[30] Foreign Application Priority Data

Apr. 26, 1985 [DE] Fed. Rep. of Germany ....... 3515056

[51] Int. Cl.⁴ ............................................ B65G 43/02
[52] U.S. Cl. .................... 198/810; 198/856; 198/496; 250/223 R
[58] Field of Search ...................... 198/496, 810, 856; 250/223 R

[56] References Cited

U.S. PATENT DOCUMENTS

| | | | |
|---|---|---|---|
| 2,732,058 | 1/1956 | Nigra et al. | 198/839 |
| 3,212,631 | 10/1965 | Thompson | 198/496 |
| 3,765,777 | 10/1973 | Williams, Jr. | 356/200 |
| 4,464,654 | 8/1984 | Klein | 198/856 X |
| 4,603,778 | 8/1986 | Thompson | 198/856 X |

FOREIGN PATENT DOCUMENTS

| | | | |
|---|---|---|---|
| 2413543 | 10/1975 | Fed. Rep. of Germany | 198/810 |
| 2812796 | 9/1979 | Fed. Rep. of Germany | 198/810 |
| 153671 | 1/1982 | German Democratic Rep. | 198/810 |
| 216214 | 12/1984 | German Democratic Rep. | 198/856 |
| 161209 | 12/1981 | Japan | 198/810 |
| 911176 | 11/1962 | United Kingdom . | |
| 1340232 | 12/1973 | United Kingdom . | |
| 1575140 | 9/1980 | United Kingdom . | |

Primary Examiner—Stephen J. Novosad
Assistant Examiner—John F. Letchford
Attorney, Agent, or Firm—Peter K. Kontler

[57] ABSTRACT

The presence of protruding filaments in a woven endless belt for the transport of tobacco or filter material in a machine of the tobacco processing industry is detected by one or more optoelectronic detectors. Signals which are generated by such detectors are evaluated to transmit a defect signal only when the detectors generate signals which were in fact initiated by protruding filaments rather than by projecting particles of tobacco or filter material, and when the number of such signals per length of the belt reaches a preselected value which warrants the generation of a defect signal.

17 Claims, 6 Drawing Figures

Fig.6

APPARATUS FOR MONITORING THE CONDITION OF FILAMENTARY BELTS IN CIGARETTE MAKING MACHINES AND THE LIKE

CROSS-REFERENCE TO RELATED APPLICATION

Figure 2:
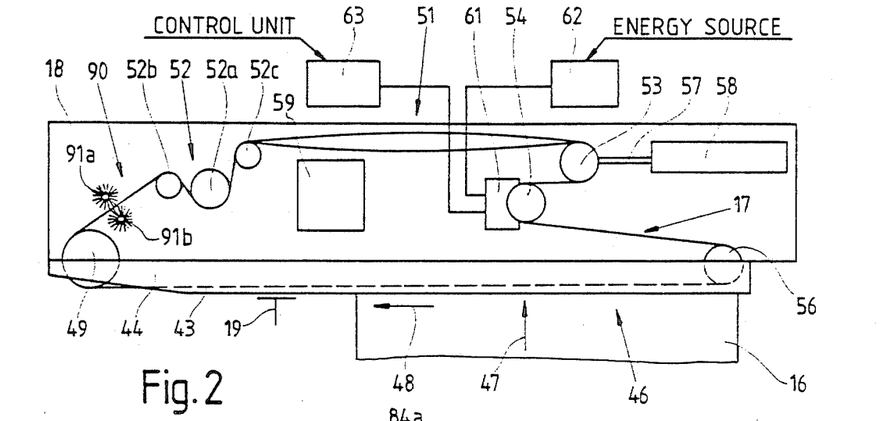
FIG. 2 is an elevational view of a detail in the machine of FIG. 1, showing the path for the endless belt conveyor, the improved apparatus and means for feeding particles of comminuted tobacco leaves to the underside of the lower reach of the conveyor.

The mounting the belt conveyor in FIG. 2 of the present application is similar to that disclosed in the commonly owned copending patent application Ser. No. 672,585 filed Nov. 16, 1984 by Alfred Hinzmann.

BACKGROUND OF THE INVENTION

The present invention relates to apparatus for monitoring the condition of endless belts which consist of or contain a filamentary material. More particularly, the invention relates to improvements in apparatus for monitoring the condition of endless belts of woven textile or other filamentary material which can be utilized in the tobacco processing industry to transport streams of particles consisting of natural tobacco, reconstituted tobacco, imitation tobacco and/or filter material. Still more particularly, the invention relates to improvements in apparatus which can be utilized with advantage to monitor the condition of foraminous belt conveyors, particularly of the type commonly used in cigarette rod making machines to transport endless streams of fragmentized tobacco leaves.

The endless belt conveyor which is utilized in a cigarette rod making machine to build up and transport a continuous stream of fragmentized smokable material is subjected to pronounced stresses, particularly in a modern high-speed cigarette maker which turns out in excess of 8,000 plain cigarettes per minute. As a rule, particles of smokable material are showered onto one side of the running belt conveyor while the other side travels along a perforated wall forming part of a suction chamber so that the showered particles are attracted to the one side and advance with the belt conveyor. Such conveyor is trained around numerous pulleys and is tensioned so as to ensure predictable advancement of its particle-conveying reach along a predetermined path. The tensioning device subjects the belt conveyor to pronounced stresses, and additional stressing of the belt conveyor takes place during travel between closely adjacent sidewalls in the tobacco channel as well as during flexing at the wrapping station where the stream of smokable material is draped into a web of cigarette paper or the like. The belt conveyor is caused to travel at an elevated speed, particularly in a modern cigarette maker, so that its life span is relatively short. It has been found that discrete filaments of a textile belt conveyor are likely to undergo extensive wear and to ultimately break as a result of the aforediscussed tensioning in a cigarette maker. The end portions of broken filaments project from the belt conveyor and are likely to interfere with proper transport of smokable material and particularly with predictable transfer of successive increments of a continuous stream of smokable material from the belt conveyor onto another conveyor. At the aforementioned operating speeds, even a short-lasting interruption of or interference with the operation of the stream forming unit in a cigarette maker can entail huge losses in output.

OBJECTS AND SUMMARY OF THE INVENTION

An object of the invention is to provide a novel and improved apparatus which can reliably monitor the condition of an endless filamentary belt conveyor and to generate signals denoting the condition of the conveyor so as to enable the attendants to inspect and, if necessary, replace the conveyor before the machine using the conveyor turns out unsatisfactory products.

Another object of the invention is to provide a novel and improved method of detecting the presence or absence of filaments projecting from a woven textile belt conveyor which is used in a cigarette making machine, a filter rod making machine or another machine of the tobacco processing industry.

A further object of the invention is to provide an apparatus which can be readily installed in existing tobacco processing machines and whose operation can be automated to any desired extent.

An additional object of the invention is to provide a machine which embodies the above outlined apparatus.

Still another object of the invention is to provide an apparatus which can readily and reliably discriminate between actual defects of the belt conveyor on the one hand and projecting fragments of tobacco or filter material on the other hand so as to avoid unnecessary generation of defect signals.

A further object of the invention is to provide the apparatus with novel and improved means for evaluating and processing the signals which are generated on detection of actual or presumable defects of a running endless belt conveyor of filamentary material.

The apparatus of the present invention can be utilized to monitor the condition of a driven endless belt conveyor which travels along a predetermined path and contains filaments. More particularly, the apparatus can be utilized to monitor the condition of a belt conveyor which transports fibrous material of the tobacco processing industry. The improved apparatus comprises a monitoring unit including at least one detector having a radiation source (for example, a source of visible light) which is arranged to emit at least one beam of radiation substantially transversely of the path and closely adjacent a portion of the belt conveyor so that a filament which protrudes from and is thus indicative of a defect of the belt conveyor influences the beam. The one detector further comprises an optoelectronic transducer or other suitable means for generating a signal in response to such influencing of the beam. The detector can further comprise means (such as a hole-type diaphragm) which is designed to shape the beam so that the diameter of the shaped beam at least approximates the diameter of a filament in the belt conveyor. The source can include means for emitting a beam in substantial parallelism with or close to the inner or outer surface of the belt conveyor which advances along the endless path.

The apparatus preferably further comprises a deflector which defines an arcuate portion of the path for the belt conveyor, and the monitoring unit can include the one detector as well as a second detector which is spaced apart from the one detector in the direction of travel of the belt conveyor along its path. The mutual positions of beams which are emitted by the radiation sources of the two detectors are such that a filament which influences the beam of the one detector thereupon influences the beam of the second detector with a delay which is a function of the length of the interval of time elapsing during transport of the filament from the one detector to the second detector. At least one of these detectors is or can be adjacent to the deflector. Such deflector can constitute a rotary pulley for the belt conveyor.

The apparatus further comprises control means having means for evaluating the signals which are transmitted by the signal generating means of the detector or detectors. The evaluating means can comprise means for transmitting defect signals when the signal generating means of the second detector generates a signal with the aforementioned delay following the generation of a signal by the signal generating means of the one detector.

Alternatively, the evaluating means can include means for transmitting defect signals in response to renewed generation of signals by a single signal generating means at a frequency which corresponds to that of circulation of a filament of the belt conveyor along its path.

The evaluating means can comprise means for transmitting timing pulses at a frequency which is a function of the speed of movement of the belt conveyor along its path. Such timing pulse transmitting means can include the aforementioned rotary pulley for the belt conveyor. The evaluating means is arranged to evaluate the signals from the signal generating means as a function to the frequency of timing pulses.

The arrangement may be such that the monitoring means comprises at least one detector adjacent to the outer side of the belt conveyor in the aforementioned path, and at least one detector adjacent to the inner side of such belt conveyor. Furthermore, the monitoring means can include one or more additional detectors which generate signals to indicate the presence or absence of filaments projecting from the one and/or other edge face of the travelling belt conveyor.

The evaluating means preferably includes means (such as a suitable counter) for transmitting a defect signal only in response to reception of a predetermined number of signals from the signal generating means during an interval of time which elapses while a filament of the belt conveyor completes a lap along its path. This prevents repeated counting of one and the same signal from the signal generating means of a detector. The signal transmitting means can comprise a resettable signal counter, and the evaluating means embodying such resettable counter then further comprises means for generating for the counter resetting signals at a frequency corresponding to that of circulation of a filament of the belt conveyor along the endless path so that the signal transmitting means transmits a defect signal only when the number of signals which are received from the signal generating means exceeds a preselected number during the interval of time which elapses between the generation of two consecutive resetting signals.

The improved monitoring apparatus preferably further comprises means for removing impurities from the aforementioned portion of the belt conveyor before such portion reaches the beam or beams of the detector or detectors. For example, the removing means can comprise one or more rotary brushes which sweep fragments of tobacco and/or dust and/or filter material away from the respective surface or surfaces of the belt conveyor before the thus cleaned portion of the belt conveyor reaches the monitoring unit. Such arrangement ensures that particles of tobacco and/or filter material which happen to adhere to the belt conveyor and project from its inner or outer side are less likely to generate or entail the generation of defect signals.

The defect signals can be utilized to generate audible and/or visible signals which warn the attendants or to arrest the machine in which the belt conveyor is put to use.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

DESCRIPTION OF THE PREFERRED EMBODIMENTS

Figure 1:
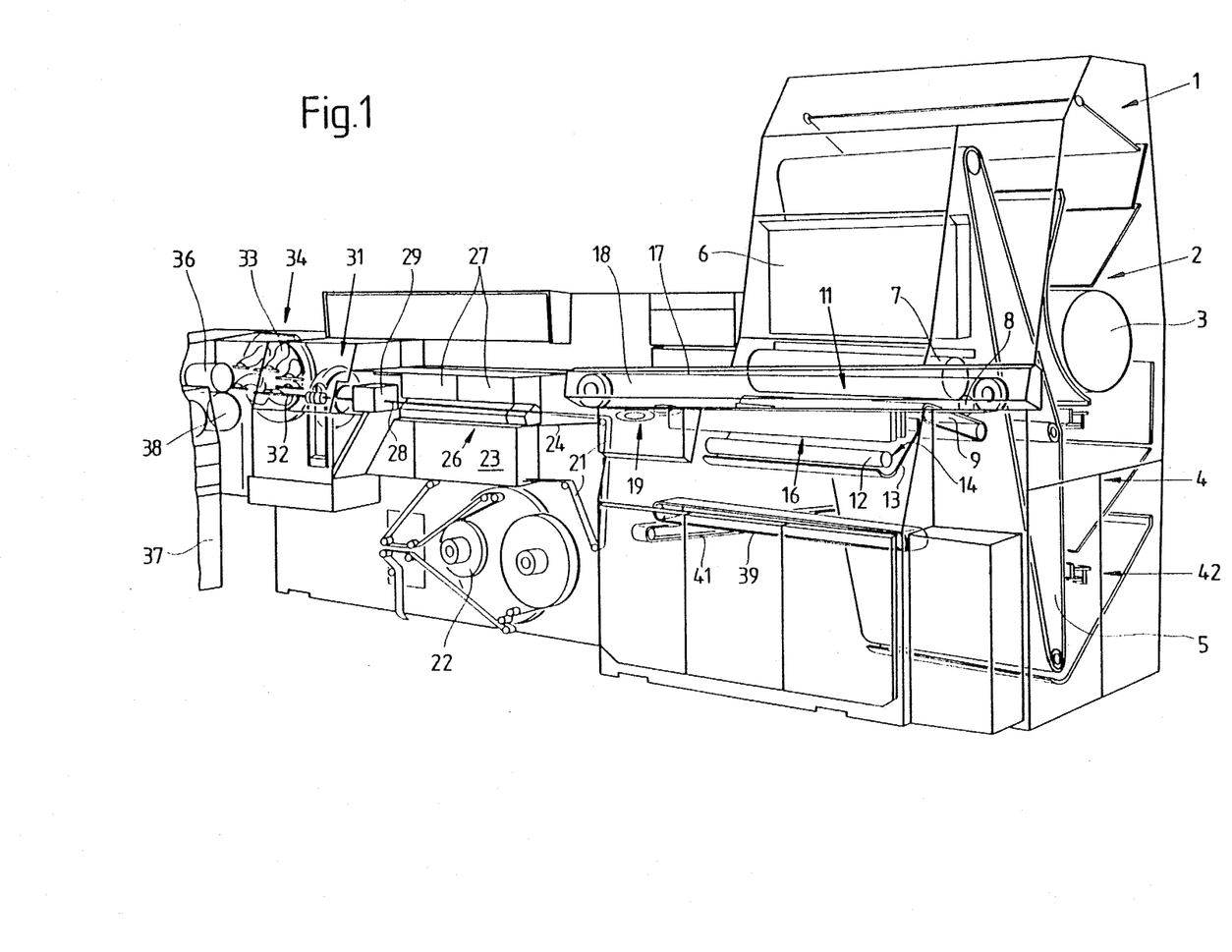
FIG. 1 is a perspective view of a cigarette rod making machine embodying an apparatus which is constructed in accordance with one feature of the present invention and monitors the condition of the endless belt conveyor which accumulates a continuous stream of fragmentized tobacco leaves.

FIG. 1 shows a cigarette rod making machine which is manufactured by the assignee of the present application and is known as PROTOS. The machine comprises a gate 1 which is operated intermittently to admit batches of shredded tobacco particles into a first distributor section 2 wherein a rotary drum-shaped conveyor 3 transfers fragmentized tobacco particles to a magazine 4 which is adjacent to the upwardly traveling stretch of an endless elevator belt conveyor 5 having pockets (not specifically shown) which are filled with tobacco particles on their way toward the upper end of the elevator conveyor where the contents of such pockets are dumped into a gathering duct 6. The rate at which the elevator conveyor 5 delivers tobacco particles to the duct 6 is regulated so that the height of the column of accumulated tobacco particles in the duct 6 remains at least substantially constant.

The particles which constitute the lower part of the column in the gathering duct 6 are removed by a driven carded drum 7 which conveys a continuous stream of tobacco particles into the range of a rapidly driven picker roller 8. The roller 8 expels tobacco particles from the carding of the conveyor 7 and propels the particles onto the upper reach of an endless belt conveyor 9 which is driven at a constant speed. The conveyor 9 accumulates a wide carpet of tobacco particles, and the leader of such carpet is propelled against a substantially vertical air curtain which is established by a classifying device 11. The arrangement is such that the heavier particles (such as fragments of tobacco ribs) penetrate across the air curtain and are collected in a suitable intercepting receptacle (not specifically shown). Satisfactory (lightweight) particles of comminuted tobacco are deflected by the air curtain into a funnel 14 which is defined by a stationary wall 13 and a carded drum 12. The drum 12 propels tobacco particles upwardly into a duct 16 which delivers a shower of tobacco particles against the underside of the lower reach 43 (see FIG. 2) of an endless foraminous belt conveyor 17. The upper side of the lower reach of the belt conveyor 17 is adjacent to the perforated bottom wall of a stationary suction chamber 18 which ensures that the particles of the shower adhere to the underside of the lower reach 43 and form thereon a growing tobacco stream (not specifically shown) which is delivered into the range of a customary trimming or equalizing device 19 serving to remove the surplus and to convert the stream into a filler having a substantially constant cross-sectional outline. The thus obtained filler is advanced in the direction of arrow 48 (see FIG. 2) and is deposited by the lower reach 43 onto a continuous cigarette paper web 21 which is drawn from a bobbin 22.

The web 21 advances through a conventional imprinting mechanism 23 on its way onto the upper reach of an endless belt conveyor 24 serving to transport the web and the filler of tobacco particles into a wrapping mechanism 26. The mechanism 26 drapes the cigarette paper web 21 around the filler so that one marginal portion of the draped web extends outwardly and is coated with a film of adhesive by a suitable paster (not shown) before it is folded over the other marginal portion to form an elongated seam extending in the longitudinal direction of the resulting cigarette rod 28. The seam is heated by a tandem sealer 27 which increases the ability of the resulting tubular wrapper of the cigarette rod 28 to resist deforming and opening stresses during the immediately-following treatment of the rod. The density of successive increments of the filler in the rod 28 is monitored by a conventional density measuring device 29 which controls the operation of the trimming device 19. Successive increments of the rod 28 enter a conventional cutoff 31 which subdivides the rod into a file of plain cigarettes 32 of double unit length.

Successive cigarettes 32 are engaged by the orbiting arms 33 of a transfer device 34 which delivers the cigarettes into the peripheral flutes of a drum 36 forming part of a filter tipping machine 37, for example, a machine known as MAX S which is manufactured by the assignee of the present application. The drum 36 delivers successive cigarettes 32 onto a severing drum 38 cooperating with a circular knife (not specifically shown) to subdivide each cigarette 32 into two cigarettes of unit length. Such cigarettes of unit length are thereupon assembled with filter rod sections of double unit length to form filter cigarettes of double unit length. Each filter cigarette of double unit length is severed to yield two filter cigarettes of unit length. The mode of operation of the filter tipping machine 37 forms no part of the present invention.

The cigarette making machine of FIG. 1 further comprises two endless belt conveyors 39 and 41 serving to collect the surplus which is removed by the rotary element or elements of the trimming device 19 and to return the removed surplus into the lower portion 42 of the distributor below the magazine 4. The returned surplus is picked up by successive pockets of the elevator conveyor 5 for readmission into the gathering duct 6.

Referring now to FIG. 2, the stream building zone at a level above the discharge end of the duct 16 is indicated by the character 46. The direction in which the shower of tobacco particles advances toward the underside of the lower reach 43 of the endless belt conveyor 17 is indicated by the arrow 47. The stream is fully built up ahead of the trimming device 19 so that the left-hand portion of the lower reach 43 of the belt conveyor 17 transports a fully grown stream which carries the surplus (such surplus is removed by the trimming device 19) and thereupon the filler toward the location of delivery onto the cigarette paper web 21.

The belt conveyor 17 is foraminous and consists of filamentary material (such material can constitute natural or synthetic fibers or a combination of both). The lower reach 43 of the belt conveyor 17 travels in a tobacco channel 44 the upper wall of which is permeable and constitutes the bottom wall of the suction chamber 18. The location where the filler is transferred from the lower reach 43 of the belt conveyor 17 onto the cigarette paper web 21 is close to the locus of the leftmost or front pulley 49 for the belt conveyor.

The upper reach 51 of the belt conveyor 17 is driven by an advancing unit 52 including a driven roller 52a flanked by two deflecting rollers 52b and 52c. The upper reach 51 is further trained over a tensioning roller 53 whose shaft is attached to the piston rod of a fluid-operated tensioning device 58 serving to maintain the belt conveyor 17 under a predetermined tension.

The endless path for the belt conveyor 17 is further defined by two additional pulleys 54 and 56. In accordance with one feature of the invention, the pulley 54 is immediately adjacent to a monitoring apparatus 61 which is constructed in accordance with one embodiment of the present invention. The arrangement is such that the pulley 54 deflects the corresponding portion of the belt conveyor 17 through angle of approximately 180 degrees.

The major part of the belt conveyor 17 is confined in the interior of the suction chamber 18.

FIG. 2 further shows that a portion of the belt conveyor 17 between the deflecting roller 52c of the advancing unit 52 and the tensioning roller 53 is twisted about it longitudinal axis through an angle of 180 degrees. The reasons for such twisting are fully disclosed in the aforementioned copending patent application Ser. No. 672,585 of Alfred Hinzmann. Twisting of the belt conveyor 17 is desirable and advantageous primarily because it ensures that, during each cycle, a different side of the belt conveyor is presented to the shower of tobacco particles which are delivered by the duct 16. This ensures that smaller tobacco particles and particles of dust which settle in the pores of the belt conveyor 17 during the preceding cycle can be sucked into the chamber 18 during the next-following cycle. The reference character 59 indicates the intake of the suction chamber 18. Such intake is connected to the inlet of a fan (not shown) or another suitable suction generating device.

The monitoring apparatus 61 is connected with a source 62 of electrical energy and such apparatus includes a control unit 63 having means for evaluating signals which are generated by the monitoring unit.

Figures 3, 4:
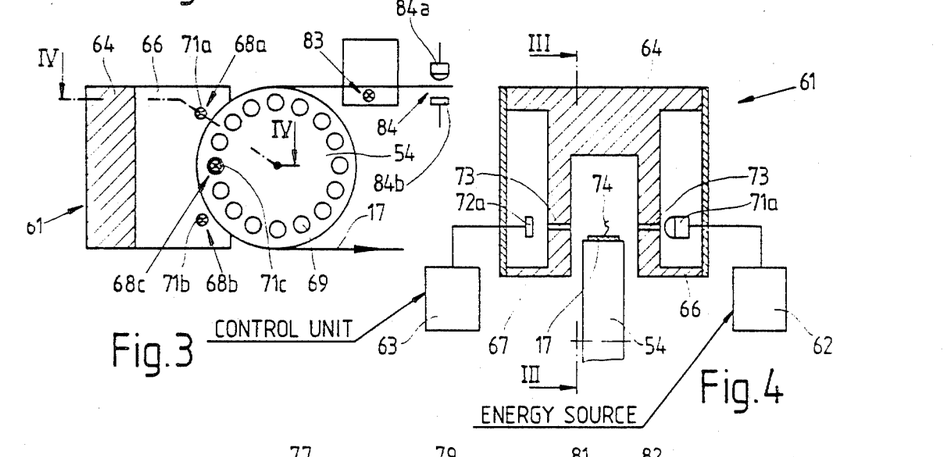
FIG. 3 is an enlarged sectional view of the improved apparatus as seen in the direction of arrows from the line III—III of FIG. 4.
FIG. 4 is a sectional 4 view as seen in the direction of arrows from the lines IV—IV in FIG. 3.
Figure 5:
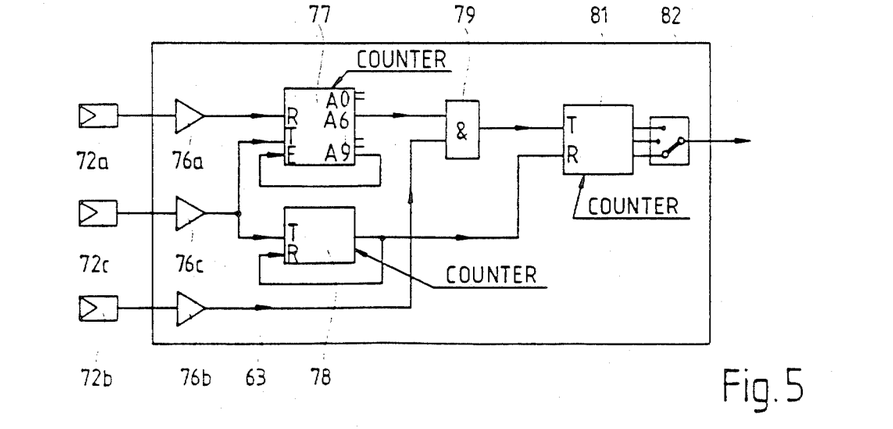
FIG. 5 is a block diagram of the evaluating circuit in the apparatus of FIGS. 1 to 4.

The details of the monitoring apparatus 61 are shown in FIGS. 3, 4 and 5. This apparatus comprises a housing 64 having two spaced-apart parallel walls 66, 67 which flank a portion of the pulley 54 for the belt conveyor 17. The monitoring unit of the apparatus 61 comprises three detectors 68a, 68b and 68c. Each of these detectors comprises a radiation source, for example a source of visible light. FIG. 4 shows the radiation source 71a of the detector 68a and its connection to the energy source 62. All three radiation sources 71a, 71b and 71c (of the detectors 68a, 68b and 68c) are shown schematically in FIG. 3. The detectors 68a and 68b are closely adjacent to that portion of the belt conveyor 17 which is trained around the pulley 54. The radiation sources 71a and 71b direct beams of radiation transversely of the path of the belt conveyor 17 and in parallel to the adjacent portions of the external surface of the belt conveyor. The detector 68c includes the pulley 54. To this end, the pulley 54 is formed with an annulus of equidistant holes 69 which are disposed between the radiation source 71c of the detector 68c and a signal generating transducer 72c. The transducer 72c generates signals whenever it is reached by the beam of radiation issuing from the respective source 71c.

The radiation sources 71a, 71b and 71c are installed in the wall 66 of the housing 64, and the respective signal generating transducers 72a, 72b and 72c are installed in the wall 67. All three radiation sources are connected to the energy source 62, and the outputs of all three transducers are connected to the corresponding inputs of the control unit 63 of the monitoring apparatus 61. In order to properly condense the beams which issue from the radiation sources 71a and 71b, the housing 64 is formed with suitable beam shaping means or diaphragms in the form of holes 73 machined into or otherwise formed in the walls 66 and 67 in line with the respective radiation sources 71 and the respective transducers 72. One of such beam shaping means or diaphragms is shown in FIG. 4 between the radiation source 71a and the associated transducer 72a. FIG. 4 also shows that the condensed beam of radiation which propagates itself from the right-hand hole 73 to the left-hand hole 73 is closely adjacent to the external surface of the deflected portion of the conveyor 17. Such beam can be interrupted by the protruding end portion 74 of a filament which forms part of the belt conveyor 17 and projects from its outer surface. The dimensions of the holes 73 are preferably selected in such a way that the diameter of the condensed beam whose path is adjacent to the external surface of the belt conveyor 17 equals or approximates the diameter of a filament in the belt conveyor. For example, the diameter of the beam which can be interrupted by the portion 74 of a filament can be a fraction of 1 mm. It has been found that a beam having a diameter of 0.4 mm is quite satisfactory for detection of portions of filaments which are customarily employed in a belt conveyor serving as a means for building up and for transporting a stream of shredded tobacco particles.

The details of the control unit 63 of the monitoring apparatus 61 are shown in FIG. 5. The output of the transducer 72a of the detector 68a is connected with an amplifier 76a whose output is connected with the reset input R of a counter 77. The counting input T of the counter 77 is connected with the output of the transducer 72c of the detector 68c by way of an amplifier 76c. The output of the amplifier 76c is further connected with the counting input of a pulse counter 78. The output of the counter 77 is connected with one input of an AND gate 79 the other input of which is connected with the output of the transducer 72b of the detector 68b by an amplifier 76b. The output of the AND gate 79 is connected with the counting input T of a resettable counter 81 which constitutes a means for transmitting defect signals. The reset input R of the counter 81 is connected with the output of the pulse counter 78. The reference character 82 denotes a selector switch which can adjust the counter 81 so as to determine the number of signals which must be received at its input T before the output of this counter transmits a defect signal. Such defect signal can be displayed for observation by the attendants, or it can be utilized to shut off the machine in which the belt conveyor 17 is used. The arrangement is such that the number of signals which the counter 81 must receive before it transmits a defect signal is selected per cycle of the belt conveyor 17, namely per interval of time which elapses during travel of any selected filament or filament portion 74 of the belt conveyor 17 along the endless path which is shown in FIG. 2.

The mode of operation of the monitoring apparatus 61 is as follows:

It is assumed that a portion 74 of a filament protrudes from the outer side of the belt conveyor 17 and that such portion 74 has been detected by the detector 68a because it has interrupted the beam of radiation between the registering holes 73 of the walls 66, 67 shown in FIG. 4. This has induced the transducer 72a of the detector 68a to transmit a signal to the reset input R of the counter 77 by way of the amplifier 76a. The counter 77 can constitute a decimal counter with ten decoding outputs A0 to A9 (for example, of the type CMOS 4017 of Motorola). The signal which is transmitted by the amplifier 76a resets the counter 77 to zero. This enables the counter 77 to count the pulses which are transmitted to its input T by the amplifier 76c, i.e., signals which are generated by the transducer 72c of the detector 68c including the pulley 54. This causes the counter 77 to transmit successive signals at its outputs A0, A1 (not shown) and so forth down to the output A9. The transducer 72c generates timing pulses at a frequency which corresponds to the speed of the belt conveyor 17, namely at intervals corresponding to predetermined increments of the length of the conveyor 17 and being determined by the mutual spacing of neighboring holes 69 in the pulley 54. This enables the second detector 68b to ascertain whether or not the defect (protruding portion 74 of a filament of the conveyor 17) has advanced within the expected interval of time from the radiation source 71a to the radiation source 71b so that it enables the detector 68b to transmit to the control unit 63 a signal with a delay corresponding to the distance between the detectors 68a and 68b.

In the embodiment which is shown in FIGS. 3 to 5, the distance between the detectors 68a and 68b is such that the transducer 72b must generate a signal with a delay which the transducer 72c requires to transmit a total of seven successive pulses to the input T of the counter 77, i.e., the output A6 must transmit a signal if the defect which has caused the detector 68a to generate a first signal has also caused the detector 68b to generate a signal with an appropriate delay. At such time, the output of the transducer 72b transmits a signal to the corresponding input of the AND gate 79 by way of the amplifier 76b so that the output of the AND gate 79 can transmit a signal to the input T of the counter 81. The counter 81 counts the number of signals which are transmitted thereto by the AND gate 79 and transmits a defect signal only if its reset input R does not receive a signal from the pulse counter 78 before its input T receives that number of signals which has been selected by the switch 82. As mentioned before, a defect signal can be displayed to the attendants to indicate that the belt conveyor 17 exhibits a defect or a selected number of defects serious enough to warrant consideration, either for inspection or for replacement of the belt conveyor. The counter 81 can be identical with or similar to the counter 77.

The purpose of the pulse counter 78 is to prevent one and the same defect of the belt conveyor 17 from generating a succession of signals which would eventually induce the counter 81 to generate a defect signal even though the generation of such defect signal is not warranted in view of the condition of the belt conveyor and setting of the switch 82. The output of the pulse counter 78 is set to transmit a signal in response to reception of a predetermined number of pulses by its input T, i.e., in response to generation of a predetermined number of successive signals by the transducer 72c of the detector 68c. The number of pulses which must be transmitted to the input T of the counter 78 before the output of this pulse counter transmits a signal is indicative of the length of the belt conveyor 17. When such number of pulses is reached, the output of the pulse counter 78 transmits a signal to the input R of the counter 81 so that the counter 81 is reset to zero. At the same time, the output of the pulse counter 78 transmits a signal to its own reset input R so that it is also reset to zero and begins to count, anew, the number of successive pulses which are transmitted thereto by the output of the transducer 72c. It will be seen that the pulse counter 78 prevents one and the same defect of the belt conveyor 17 from causing the generation of a succession of signals which would be transmitted to the counter 81 before this counter is reset to zero. The switch 82 selects the density or total number of signals which must be received from the AND gate 79 during circulation of any selected point on the belt conveyor 17 along the endless path for this conveyor before the counter 81 transmits a defect signal.

The purpose of the second detector 68b is to verify the authenticity of signals which are generated by the transducer 72a of the first detector 68a. For example, if the belt conveyor 17 carries an outwardly projecting fragment of tobacco, such fragment acts not unlike the portion 74 of the filament shown in FIG. 4, namely it induces the transducer 72a to generate a signal which is transmitted to the reset input R of the decimal counter 77. The falsity of such signal is detected by the detector 68b if the tobacco fragment which has induced the transducer 72a to generate a signal is ejected by centrifugal force during travel along that arcuate portion of the path which is defined by the pulley 54, i.e., if such fragment is prevented from reaching the beam between the radiation source 71b and the registering transducer 72b.

A similar verification is necessary if the first detector 68a is induced to generate a signal in response to detection of a floating speck of dust or a floating particle of tobacco. Such speck of dust or such particle of tobacco is highly unlikely to reach the detector 68b with the requisite delay, namely in exact imitation of the travel of a point on the conveyor 17 from a position of registry with the diaphragm of the detector 68a to a position of registry with the diaphragm of the detector 68b. The input of the counter 81 of the unit 63 shown in FIG. 5 will receive a signal only if both inputs of the AND gate 79 receive signals at the same time, namely a first signal from the output A6 of the counter 77 and a second signal directly from the amplifier 76b, i.e., from the transducer 72b of the second detector 68b. If the upper input of the AND gate 79 of FIG. 5 receives a signal from the output A6 but the lower input of such AND gate does not receive a signal from the amplifier 76b, the counter 77 continues to transmit signals at its successive outputs A7, A8 and A9. The signal from the output A9 is transmitted to the enabling input E which arrests the counter 77. The counter 77 is started again only when its reset input R receives a signal from the amplifier 76a.

The selector switch 82 constitutes a desirable and advantageous feature because it enables the operator to select that number of signals from the AND gate 79 which is necessary to induce the counter 81 to transmit a defect signal. Otherwise, the presence of a relatively small defect or the presence of two or more minor defects on the belt conveyor 17 could entail the generation of a premature defect signal.

It will be readily appreciated that the monitoring apparatus 61 can be used with equal or similar advantage to ascertain the condition of the belt conveyor 24 of FIG. 1 or the condition of the conveyor 5, 9, 39 or 41 of FIG. 1. Furthermore, similar monitoring apparatus can be utilized in other types of machines which are used for the processing of tobacco and related materials, for example, in a filter rod making machine which invariably employs one or more endless flexible belt conveyors made of or containing a filamentary material.

Furthermore, though the detector 68c of FIG. 2 embodies the pulley 54, it is clear that this detector can employ or can be combined with any other means which enables it to generate pulses at a frequency denoting the speed of travel of the conveyor 17 along its endless path.

If the belt conveyor 17 or another monitored conveyor is not mounted in a manner as shown in FIG. 2 between the rollers 52c and 53, namely if a portion of its return reach 51 is not twisted through an angle of 180 degrees, it may be desirable to provide the monitoring apparatus 61 with at least one additional detector (shown at 83 in FIG. 3) which is mounted in such a way that the beam issuing from its radiation source extends transversely of the path of movement of the conveyor 17 adjacent to the inner or rear side of the conveyor. The detector 83 can be identical with the detector 68a or 68b. The control unit 63 is then modified so that it can process signals which are generated by the transducer of the detector 83 or, alternatively, the modified monitoring apparatus which includes a detector 83 can comprise a second control unit (analogous to the control unit 63 of FIG. 5) which receives signals from the transducer of the detector 83.

It is further possible to monitor one or both edge faces of the belt conveyor 17. For example, the monitoring apparatus 61 can comprise at least one additional detector 84 having a radiation source 84a and a transducer 84b. The radiation source 84a can include or can cooperate with a suitable diaphragm which condenses the beam (e.g., a beam of visible light) so that such beam traverses the plane of the respective reach or stretch of the conveyor 17 in immediate or close proximity of the selected edge face. Thus, the detector 84 can ascertain the presence or absence of filaments which protrude from the respective edge face of the conveyor 17 and to generate appropriate signals which are transmitted to the control unit 63 of FIG. 5 or to discrete control unit, not shown. A single additional detector 84 will suffice if the reach 51 of the belt conveyor 17 is twisted through 180 degrees in a manner as shown in the upper portion of FIG. 2. This will be readily appreciated since the detector 84 then successively monitors alternate edge faces of the belt conveyor 17. If the designer of the apparatus 61 decides that the apparatus should monitor the belt conveyor 17 for the presence of absence of defects along one or both edge faces of the belt conveyor, the apparatus can be equipped with pairs of additional detectors 84, one pair for each edge face, and the corresponding control unit is designed and operates in the same way as described in connection with FIG. 5, i.e., signals which are generated by one detector 84 of each pair are verified by the other detector of the respective pair so as to ensure that the counter 81 of such control unit receives signals only when each signal has been verified as a genuine signal rather than a signal which is generated by a floating particle of tobacco or a speck of dust.

Figure 6:
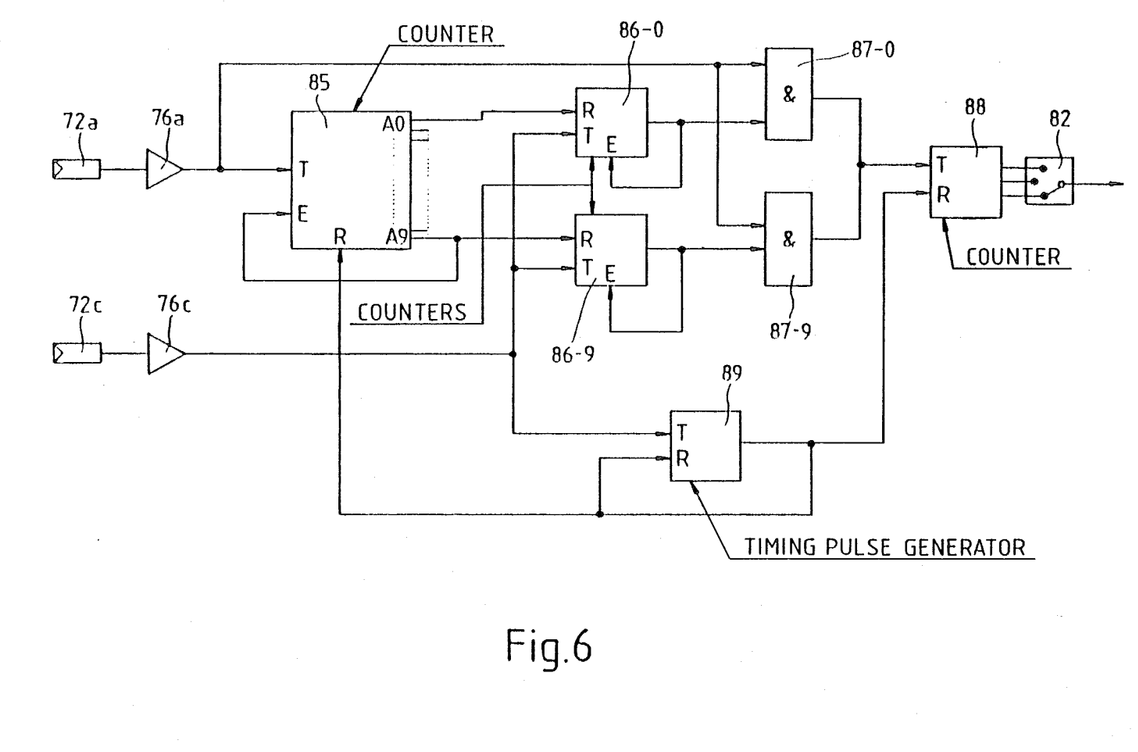
FIG. 6 is a block diagram of a modified evaluating circuit.

FIG. 6 shows a modified control unit which can be utilized instead of the control unit 63 of FIG. 5. The control unit of FIG. 6 need not receive signals from a second detector of defects on the monitored belt conveyor, i.e., the second detector 68b of FIG. 3 can be omitted. The transducer 72a of FIG. 6 forms part of a detector corresponding to the detector 68a of FIG. 3, and the transducer 72c of FIG. 6 corresponds to the similarly referenced transducer 72c of the detector 68c. The output of the transducer 72a shown in FIG. 6 is connected with the counting input T of a decimal counter 85 by way of an amplifier 76a. The counter 85 has ten outputs A0–A9. Each of these outputs is connected with the reset input R of a discrete counter 86. FIG. 6 merely shows the first counter 86-0 which is connected with the output A0 of the counter 85, and the last or tenth counter 86-9 whose reset input R is connected with the output A9 of the counter 85. It will be seen that successive signals which are transmitted by the transducer 72a reach the reset inputs R of successive counters 86. The counters 86 are started in response to reception of signals from the respective outputs of the counter 85. The output of each counter 86 is connected with one input of a discrete AND gate 87. FIG. 6 merely shows the AND gate 87-0 which is connected with the output of the counter 86-0, and the AND gate 87-9 which is connected with the output of the corresponding counter 86-9. Actually, the control unit of FIG. 6 comprises a total of ten AND gates 87 and a total of ten counters 86. The other input of each of the ten AND gates 87 is connected directly with the output of the amplifier 76a. The output A9 of the counter 85 is connected with its enabling input E, and the output of each of the counters 86 is further connected to the respective enabling input E. The output of the amplifier 76c is connected to the counting inputs T of all ten counters 86 as well as to the counting input T of a timing pulse generator 89. The outputs of all ten AND gates 87 are connected to the counting input T of a resettable signal counter 88 which constitutes a means for transmitting defect signals for display or for other purposes. The reset input R of the counter 88 is connected with the output of the timing pulse generator 89, and the output of this timing pulse generator is further connected to its own reset input R as well as to the reset input R of the counter 85. The number of signals which the input T of the counter 88 must receive from the AND gates 87 before its output transmits a defect signal is selected by a switch 82 in the same way as described in connection with FIG. 5. The counter 88 can be identical with the counter 81 of FIG. 5, and the decimal counter 85 of FIG. 6 can be identical with or analogous to the counter 77 of FIG. 5. The timing input T of the timing pulse generator 89 is connected with the output of the amplifier 76c so that the pulse generator 89 counts successive signals which are generated by the transducer 72c of the detector corresponding to the detector 68c of FIG. 3.

The construction of the counters 86 is such that, when the output of a counter 86 transmits a signal, the signal is transmitted not only to the corresponding input of the associated AND gate 87 but also to the enabling input E of the same counter 86 whereby the counter 86 is stopped. Such counter is started again only in response to reception of a signal at its input R, namely from the corresponding output of the counter 85. The counter 85 is automatically arrested when its output A9 transmits a signal to its enabling input E. This means that the counter 85 is started again only in response to reception of a signal from the transducer 72a by way of the amplifier 76a.

In operation, successive signals which are transmitted by the transducer 72a and are amplified by the amplifier 76a reach the input T of the counter 85. Such signals are transmitted sucessively to the outputs A0–A9 so that they reach in inputs R of the associated counters 86. If the signal which is transmitted to the input R of the counter 86-0 of FIG. 6 is a signal which was generated by a truly defective portion of the belt conveyor 17 or another belt conveyor, such signal must be generated again after a certain interval of time, namely when such signal again reaches the detector including the transducer 72a of FIG. 6. The input T of the counter 86-0 receives pulses from the transducer 72c, and the counter 86-0 counts such pulses for the purpose of delaying the transmission of a signal which was received from the output A0 of the counter 85 to the input R of the counter 86-0.

When the counter 86-0 has received from the transducer 72c a predetermined number of pulses, namely a number which corresponds to the full length of the belt conveyor 17 or another monitored conveyor, the output of the counter 86-0 transmits a signal to the corresponding input of the associated AND gate 87-0. At the same time, the defect which has first caused the transmission of a signal to the input R of the counter 86-0 will again cause the generation of a signal by the transducer 72a upon completed travel of the defect along the full length of the path for the monitored conveyor. The newly generated signal is transmitted via amplifier 76a directly to the other input of the AND gate 87-0 so that the output of the AND gate 87-0 transmits a signal to the input T of the counter 88 only if the first received signal is followed by a further signal after elapse of an interval of time corresponding to the interval which is required by any selected point of the belt conveyor 17 or another monitored belt conveyor to cover the entire endless path for such belt conveyor. At the same time, the output of the counter 86-0 transmits a signal to its enabling input E which arrests the counter 86-0 so that the latter is inactive and is started again only in response to reception of a fresh signal at the input R, namely from the output A0 of the counter 85.

A further signal which the transducer 72a transmits via amplifier 76a and reaches the input T of the counter 85 is transmitted to the next output A1 (not specifically referenced in FIG. 6), and such signal is then transmitted to the second counter 86-1 (not shown in FIG. 6) for the same purpose as described above in connection with the counter 86-0. The second counter 86-1 transmits to the associated AND gate 87-1 (not shown in FIG. 6) a signal after elapse of the interval of time as described above in connection with the AND gate 87-0. The mode of operation of the remaining eight counters 86-2 to 86-9 and of the associated AND gates 87-2 to 87-9 is the same as described above. The counters 86 can be replaced with other types of time-delay elements, for example, with shift registers.

The tenth signal from the transducer 72a during circulation of any selected point of the monitored conveyor along the endless path is transmitted not only to the reset input R of the corresponding counter 86-9 but also to the enabling input E of the counter 85 so that the counter 85 is arrested. The signal which has been transmitted to the input R of the counter 86-9 is verified in the same way as described above in connection with the counter 86-0, i.e., the output of the counter 86-9 transmits a signal to the corresponding input of the associated AND gate 87-9 with that predetermined delay which is required any selected point of the monitored conveyor to cover the endless path. The timing pulse generator counts the number of pulses which are transmitted by the transducer 72c via amplifier 76c. The setting of the pulse generator 89 is such that its output transmits a signal when its input T receives a number of pulses corresponding to the length of the monitored conveyor. At such time, the output of the timing pulse generator 89 transmits a signal to the reset input R of the counter 88 so that the counter 88 is reset to zero. At the same time, the output of the timing pulse generator 89 transmits a signal to its own input R so that the timing pulse generator is also reset to zero. The just described undertaking ensures that the counter 88 does not repeatedly receive signals denoting one and the same defect. The counter 88 transmits a defect signal only if it receives from the AND gates 87-0 to 87-9 a predetermined number of signals within that interval of time which is required by a defect of the belt conveyor 17 or another monitored belt conveyor to cover the entire endless path for such conveyor.

The signal which appears at the output of the timing pulse generator 89 also reaches the reset input R of the counter 85 so that this counter is reset to zero in order to prevent the transmission of signals which would again denote the same defects as during the preceding cycle of the monitored conveyor.

Referring again to FIG. 2, the improved monitoring apparatus preferably further comprises means 90 for removing impurities from the monitored conveyor so as to reduce the likelihood of the generation of signals in response to detection of impurities rather than in response to detection of actual defects of the monitored conveyor. The impurities removing means 90 is installed in the suction chamber 18 upstream of the monitoring unit 68a 68b, 68c of the apparatus 61, namely immediately or closely downstream of the front pulley 49. The illustrated impurities removing means 90 comprises two rotary cylindrical or conical brushes 91a and 91b which are adjacent to opposite sides of the belt conveyor 17.

The provision of the removing means 90 renders it possible to dispense with the second detector 68b because the likelihood of repeated and timely generation of signals in response to detection of fragments of tobacco particles or fragments of dust by several discrete detectors (68a, 68b) is highly unlikely. In other words, if the apparatus is equipped with the impurities removing means 90 or with an analogous belt cleaning device, the provision of a second detector constitutes an optional feature. It is clear that the illustrated cylindrical or analogous rotary brushes 91a and 91b can be replaced with, or used in addition to, other suitable cleaning means such as one or more nozzles which discharge jets of compressed air, one or more mechanical scrapers or the like.

FIGS. 5 and 6 illustrate discrete elements of the respective control units by blocks and other types of symbols. Such symbols are utilized primarily for the convenience of illustration and explanation. If the apparatus is embodied in a modern high-speed cigarette making machine or another automated machine of the tobacco processing industry, the functions of individual elements which are shown in FIGS. 5 and 6 can be carried out by a computerized circuit wherein the individual elements are not distinguishable from each other. All that counts is to ensure that signals which are generated by one or more detectors are properly evaluated in order to verify the authenticity of such signals as well as to ensure that only a predetermined number of defects of a monitored conveyor will actually entail the generation of a defect signal, namely the generation of a signal which is displayed to the attendants and/or is used to effect a change in the operation of the machine employing the monitored conveyor, e.g., replacement of the defective conveyor or stoppage of the machine for the purpose of preventing the making of unsatisfactory smokers' products.

The improved monitoring apparatus are susceptible of many additional modifications. For example, the detectors need not be mounted exactly in a manner as shown even though the illustrated mounting of detectors renders it possible to ensure the detection of protruding filaments with a high degree of reliability. Furthermore, the detector or detectors need not necessarily be mounted in the region of a pulley, such as the pulley 54 of FIG. 2, especially if the apparatus includes the removing means 90 or an analogous device which is capable of removing impurities and other foreign particles upstream of the location of the monitoring unit. The placing of detectors 68a and 68b adjacent the pulley 54 is desirable and advantageous, especially if the apparatus does not employ a belt cleaning device or if the likelihood of generation of signals in response to detection of floating tobacco particles and/or other foreign matter is to be reduced even further.

All embodiments of the improved monitoring apparatus exhibit the important advantage that the apparatus can detect the presence of protruding filament portions or other defects on the monitored conveyor with a high degree of reliability. This renders it possible to undertake corrective measures in good time before a defective conveyor is likely to cause the machine to turn out a large number of unsatisfactory smokers' products and/or before the defective belt conveyor can damage other parts of the machine. Another important advantage of the improved monitoring apparatus is that it can be readily installed in existing cigarette making and other machines of the tobacco processing industry. A further important advantage of the improved monitoring apparatus is that it can be readily designed in such a way that it generates a defect signal only when the defect or defects of the monitored conveyor are sufficiently serious to warrant attention by the person in charge, e.g., to inspect the belt conveyor or to arrest the machine.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. In a machine for making smokers' products, a driven foraminous belt conveyor which contains filaments and is arranged to transport fibrous matrial of the tobacco processing industry; guide means defining for the conveyor a predetermined path; and apparatus for monitoring the condition of the conveyor, comprising a monitoring unit including at least one detector having a radiation soucre arranged to emit at least one beam of radiation substantially transversely of said path and closely adjacent a portion of the conveyor so that a filament which projects from and is thus indicative of a defect of said portion of the conveyor influences said beam, and means for generating a signal in response to such influencing of the beam by the filament of the driven conveyor.

2. The structure of claim 1, wherein said conveyor includes a belt conveyor which contains filaments having a predetermined diameter, said at least one detector further comprising means for shaping the beam so that the diameter of the shaped beam at least approximates said predetermined diameter.

3. The structure of claim 1, wherein said conveyor has an exposed surface and said source includes means for emitting a beam in substantial parallelism with and close to the surface of the conveyor which travels along said path.

4. The structure of claim 1, wherein said guide means comprises a deflector which defines an arcuate portion of said path, said monitoring unit including said one detector and a second detector which is spaced apart from said one detector in the direction of travel of the conveyor along said path, the mutual positions of beams which are emitted by the radiation sources of said detectors being such that a filament which influences the beam of said one detector thereupon influences the beam of said second detector with a delay which is a function of the length of the interval of time elapsing during transport of such filament from the one detector to the second detector, at least one of said detectors being adjacent said deflector.

5. The structure of claim 4, wherein said deflector includes a rotary pulley for the conveyor.

6. The structure of claim 4, wherein said apparatus further comprises control means having means for evaluating the signals from the signal generating means of said detectors and means for transmitting defect signals when the signal generating means of said second detector generates a signal with said delay following the generation of a signal by the signal generating means of said one detector.

7. The structure of claim 1, wherein said apparatus further comprises control means having means for evaluating said signals and including means for transmitting defect signals in response to renewed generation of signals by said signal generating means at a frequency corresponding to that of circulation of a filament of the conveyor along said path.

8. The structure of claim 1, wherein said apparatus further comprises means for transmitting timing pulses at a frequency which is a function of the speed of movement of the conveyor along said path, including a rotary pulley for the conveyor in said path, said apparatus further comprising means for evaluating said signals as a function of the frequency of said timing pulses.

9. The structure of claim 1 wherein said conveyor includes a belt conveyor having an inner side and an outer side and said source is arranged to emit the beam adjacent to one of said sides.

10. The structure of claim 1, wherein said conveyor includes an endless belt conveyor having a first side and a second side and first and second edge faces alternating with said sides, said source being arranged to emit the beam adjacent to one of said edge face.

11. The structure of claim 1, wherein said apparatus further comprises means for evaluating the signals from said signal generating means, including means for transmitting a defect signal in response to reception of a predetermined number of signals from said signal generating means during an interval of time which elapses for completion of travel of a filament of the conveyor along said path.

12. The structure of claim 11, wherein said transmitting means comprises a resettable signal counter and said evaluating means further comprises means for generating for said counter resetting pulses at a frequency corresponding to that of the circulation of a filament of the conveyor along said path so that said transmitting means transmits a defect signal only when the number of signals from said signal generating means exceeds a preselected number during the interval which elapses between the generation of two consecutive pulses.

13. The structure of claim 1, further comprising means for removing impurities from said portion of the conveyor before such portion reaches said beam.

14. The structure of claim 13, wherein said removing means comprises at least one rotary brush.

15. The structure of claim 1, wherein said at least one detector comprises a diaphragm arranged to focus the beam upon a narrow area adjacent such path.

16. The structure of claim 1, wherein said signal generating means comprises an optoelectronic transducer.

17. In a machine for making smokers' products, a driven foraminous belt conveyor which contains filaments and is arranged to transport fibrous material of the tobacco processing industry; guide means defining for the conveyor a predetermined path; and apparatus for monitoring the condition of the conveyor, comprising a monitoring unit including at least one detector having a radiation source arranged to emit at least one beam of radiation substantially transversely of said path and closely adjacent a portion of the conveyor so that a filament which projects from and is thus indicative of a defect of said conveyor influences said beam, means for generating a signal in response to such influencing of the beam by the filament of the driven conveyor, and control means for verifying the authenticity of said signal.

* * * * *